(12) United States Patent
Tsubota et al.

(10) Patent No.: US 11,033,566 B2
(45) Date of Patent: Jun. 15, 2021

(54) METHOD OF IMPROVING LACRIMAL SECRETION FOR DRY EYE TREATMENT USING MAQUI BERRY EXTRACT

(71) Applicants: ORYZA OIL & FAT CHEMICAL CO., LTD., Aichi (JP); KEIO UNIVERSITY, Tokyo (JP)

(72) Inventors: Kazuo Tsubota, Tokyo (JP); Shigeru Nakamura, Tokyo (JP); Toshihiro Imada, Tokyo (JP); Junji Tanaka, Aichi (JP); Takashi Kadekaru, Aichi (JP); Hiroshi Shimoda, Aichi (JP); Hiromichi Murai, Aichi (JP)

(73) Assignees: ORYZA OIL & FAT CHEMICAL CO., LTD., Aichi (JP); KEIO UNIVERSITY, Tokyo (JP)

( * ) Notice: Subject to any disclaimer, the term of this patent is extended or adjusted under 35 U.S.C. 154(b) by 0 days.

(21) Appl. No.: 15/725,339

(22) Filed: Oct. 5, 2017

(65) Prior Publication Data
US 2018/0036328 A1     Feb. 8, 2018

Related U.S. Application Data

(63) Continuation of application No. 14/653,283, filed as application No. PCT/JP2013/083790 on Dec. 17, 2013, now abandoned.

(30) Foreign Application Priority Data

Dec. 18, 2012  (JP) ................................. 2012-276210
Mar. 28, 2013  (JP) ................................. 2013-069773

(51) Int. Cl.
| | |
|---|---|
| *A61K 31/7048* | (2006.01) |
| *A23L 33/105* | (2016.01) |
| *A61K 36/185* | (2006.01) |
| *A61K 31/353* | (2006.01) |

(52) U.S. Cl.
CPC ........ *A61K 31/7048* (2013.01); *A23L 33/105* (2016.08); *A61K 31/353* (2013.01); *A61K 36/185* (2013.01)

(58) Field of Classification Search
None
See application file for complete search history.

(56) References Cited

U.S. PATENT DOCUMENTS

| | | |
|---|---|---|
| 6,238,673 B1 | 5/2001 | Howard |
| 2011/0268825 A1 | 11/2011 | Burgos |

FOREIGN PATENT DOCUMENTS

| | | |
|---|---|---|
| WO | 2011/048479 | 4/2011 |

OTHER PUBLICATIONS

Droault-Holowacz, S. et al "Antioxidants intake and dry eye syndrome . . . " Eur. J. Ophthalmol., vol. 19, pp. 337-342. (Year: 2009).*
Kahkonen, M. et al "Antioxidant activity of Anthocyanins and their aglycons" J. Agric. Food Chem., vol. 51, pp. 628-633. (Year: 2003).*
Uchino, Y. et al "Anew mouse model of dry eye disease . . . " Cornea, suppl. 1, pp. S63-S65. (Year: 2012).*
Nakamura, S. et al "Involvement of oxidative stress on corneal epithelial alterations . . . " Invest. Ophthalmol. Vis. Sci., vol. 48, No. 4, pp. 1552-1558. (Year: 2007).*
Nakamura, S. et al "Lacrimal hypofunction as a new mechanism in dry eye . . . " PLoS One, vol. 5, issue 6, pp. 1-10. (Year: 2010).*
Sindhu, E. et al "Antioxidant activity of carotenoid lutein . . . " Ind. J. Exp. Biol., vol. 48, pp. 843-848. (Year: 2010).*
Honma et al., "Maqui-berry, a gift . . . Polyphenol-containing Fruit", The Food Industry, Jun. 15, 2012, vol. 55, No. 11, pp. 66-68. (International Search Report as a concise explanation).
Cespedes et al., "Phytochemical profile . . . Stuntz (Elaecarpaceae)", Food Chemistry, 2010, vol. 119, Issue 3, pp. 886-895.
Kadekaru et al., "Super Fruit 'Maqui-berry' no Eye Care Kino", Journal of Japanese Council for Advanced Food Ingredients Research, Dec. 15, 2012, vol. 15, No. 2, pp. 81-84. (International Search Report as a concise explanation).
Higuchi et al., "Dry Eye . . . Oxygen Species", Journal of the Eye, 2008, vol. 25, No. 12, pp. 1639-1645. (International Search Report as a concise explanation).
Tsubota et al., "Oxidative Stress . . . Mechanism of Aging", Journal of Japanese Ophthalmological Society, 2007, vol. 111, No. 3, pp. 193-206.
Wang et al., "Maqui Berry . . . COX-2 Protein Expression", ACS Symposium Series (American Chemical Society), Mar. 6, 2012, vol. 1093, pp. 95-116.

(Continued)

*Primary Examiner* — Leigh C Maier
(74) *Attorney, Agent, or Firm* — Clark & Brody LP

(57) ABSTRACT

This invention provides a prophylactic and therapeutic agent for dry eye, having new ingredients to reduce the deterioration of the lacrimal secretory ability and to inhibit the generation of radical oxygen in lacrimal gland tissue. The prophylactic and therapeutic agent for dry eye of this invention contains the maqui berry extract as the active substance of this invention, i.e. containing delphinidin glycoside extracted from the maqui berry and at least one or more of the active substances delphinidin-3-sambubioside-5-glucoside, delphinidin-3,5-diglucoside, delphinidin-3-sambubioside and delphinidin-3-glucoside, preferably delphinidin-3,5-diglucoside.

7 Claims, 11 Drawing Sheets

(56) References Cited

OTHER PUBLICATIONS

Mousavinejad et al., "Identification and . . . Iranian cultivars", Food Chemistry, 2009, vol. 115, Issue 4, pp. 1274-1278.
Schreckinger, M. et al., "Antioxidant capacity and in vitro inhibition of adipogenesis . . . " J. Agric. Food Chem. 2010, vol. 58, pp. 8966-8976.

* cited by examiner

HPLC Chart of maqui berry extract (Fr. 1, 2, 5, 6)

Fr. 1: Delphinidin-3-sambubioside-5-glucoside

Fr. 2: Delphinidin-3, 5-diglucoside

Fr. 5: Delphinidin-3-sambubioside

Fr. 6: Delphinidin-3-glucoside

Mean+SD, n=8  LG.

*p<0.05, ***p<0.001 vs Vehicle p<0.001 vs Tempol

Mean+SD, n=8 LG.

*p<0.05, ***p<0.001 vs Vehicle

METHOD OF IMPROVING LACRIMAL SECRETION FOR DRY EYE TREATMENT USING MAQUI BERRY EXTRACT

This application is a Continuation of U.S. Ser. No. 14/653,283 filed on Jun. 18, 2015, which is a national phase of PCT/JP2013/083790 filed on Dec. 17, 2013.

TECHNICAL FIELD

This invention relates to compositions that allow the eye to increase lacrimal secretion, specifically to increase the amount of lacrimal secretion that has been lessened by functional deterioration due to an excessive use of the eyes.

TECHNICAL BACKGROUND

Lacrimal fluid is a thin layer of liquid approximately 7 μm thick that covers the outermost surface of the eyeball. Lacrimal fluid of the outermost surface consists of a three-layer structure of an oil layer, a water layer and a mucin layer. These layers influence one another in adjusting the structure of the lacrimal fluid. Each layer of the lacrimal fluid contains various ingredients such as protein including lactoferrin, lysozyme, IgA (immunoglobulin A), IgG (immunoglobulin G), albumin or the like, wax, cholesterol, glucide, mucin or the like. The function of the lacrimal fluid containing these ingredients is to keep the ocular surface moist to prevent infection from pathogens or the like that enter from the outside, also to supply a number of physiological active substances and to supply oxygen to non-vascular tissue like the cornea or the like.

As such, lacrimal liquid has various functions. However, if there are abnormalities in the lacrimal secretion, resulting in changes in the amount or quality of secretion, thus resulting in an increase in the amount of evaporation of the lacrimal liquid or the like, the lacrimal liquid may not function well. Such lacrimal abnormalities increase the cases of dry eye, such as people are now aware.

Various causes of dry eye have been reported recently. One of the more noticeable causes is the excessive viewing of visual display terminals (VDT).

Recent development of information technology and its excellent infrastructure drastically increases the opportunity to use computers in daily life. According to the estimated figure of Intel Corporation, it is said that there are about one trillion computers linked to the Internet all over the world. Today, most office workers view their work on a VDT. As computers are being frequently used, an increasing number of people are complaining of eyestrain and of symptoms of dry eye and of impaired vision, possibly caused by VDT work, which is starting to become an issue as a serious health problem in advanced industrial countries. One of the main factors in causing symptoms of dry eye is thought to be that the viewing of VDTs decreases the frequency of blinking by one fourth compared to the normal frequency, thus increasing the amount of evaporation of lacrimal liquid. The inventors of this invention also found a new factor in causing dry eye, namely, that excessive viewing of VDTs deteriorates the function of lacrimal fluid, thus decreasing the amount of secretion of lacrimal liquid.

It is suspected that excessive use of the eyes causes oxidant stress. A report (Non-patent Document 1) in 2007 by Nakamura et al said that corneal-epithelium disorder caused by viewing VDTs is induced by such oxidant stress.

To ease the discomfort of eyestrain, dry eye or the like nowadays, it is known to be effective to replace deficient lacrimal liquid by placing drops of artificial tears into the eyes or by closing the lacrimal puncta or the like. However, each of these remedies is just a temporary, supportive one and insufficient. Therefore, instead of these remedies, a way to reduce dry eye, a foreign-body feeling, eye discomfort, eyestrain or the like drastically is required by replacing lost lacrimal secretion or to have the effective compositions for the above remedies.

Dry eye is associated with radical oxygen in the lacrimal gland tissue. Thus, to prevent and cure dry eye, it is required to suppress the radical oxygen that is expressly within the lacrimal gland tissue.

PRIOR ART DOCUMENTS

Non-Patent Documents

Non-patent Document 1: Investigative Ophthalmology & Visual Science, April 2007, Vol. 48, No. 4, p 1552-1558, "Involvement of Oxidative Stress on Corneal Epithelial Alteration in a Blink-suppressed Dry Eye"

SUMMARY OF THE INVENTION

Problems to be Resolved by the Invention

On such a background, the inventors of this invention learned that maqui berry extract reduces the deterioration of lacrimal secretion and the generation of radical oxygen in lacrimal gland tissue. They found too that delphinidin glycoside, which is contained much in maqui berry extract, assumes an important role as a physiologically active substance, thus resulting in the completion of this invention. In other words, the aim of this invention is to provide a prophylactic and therapeutic agent for dry eye, having new ingredients, by which maqui berry extract or delphinidin glycoside reduces the deterioration of the lacrimal secretory ability to suppress the generation of radical oxygen in the lacrimal gland tissue.

Means of Solving the Problems

The features of this invention for solving the aforementioned problems are as follows.
1. Prophylactic and therapeutic agent for dry eye, containing maqui berry extract as an active substance.
2. Prophylactic and therapeutic agent for dry eye, containing delphinidin glycoside as an active substance, extracted from the maqui berry.
3. Prophylactic and therapeutic agent for dry eye, containing either delphinidin-3-sambubioside-5-glucoside, delphinidin-3,5-diglucoside, delphinidin-3-sambubioside or delphinidin-3-glucoside as an active substance.
4. Prophylactic and therapeutic agent for dry eye, containing delphinidin-3, 5-diglucoside as an active substance.
5. Prophylactic and therapeutic agent for dry eye, containing maqui berry extract including delphinidin-3,5-diglucocide as an active substance.
6. Inhibitor to the deterioration of the lacrimal secretory ability, containing maqui berry extract as an active substance.
7. Inhibitor to the deterioration of the lacrimal secretory ability, containing delphinidin glycoside as an active substance, extracted from the maqui berry.
8. Inhibitor to the deterioration of the lacrimal secretory ability, containing either delphinidin-3-sambubioside- 5-glucoside, delphinidin-3,5-diglucoside, delphinidin-3-sambubioside or delphinidin-3-glucoside as an active substance.

9. Inhibitor to the deterioration of the lacrimal secretory ability, containing the maqui berry extract, including delphinidin-3,5-diglucocide as an active substance.

10. Inhibitor to the generation of radical oxygen in the lacrimal gland tissue, containing the maqui berry extract as an active substance.

11. Inhibitor to the generation of radical oxygen in the lacrimal gland tissue, containing delphinidin glycoside as an active substance, extracted from the maqui berry.

12. Inhibitor to the generation of radical oxygen in the lacrimal gland tissue, containing at least one or more of delphinidin-3-sambubioside-5-glucoside, delphinidin-3,5-diglucoside, delphinidin-3-sambubioside and delphinidin-3-glucoside as an active substance.

13. Inhibitor to the generation of radical oxygen in the lacrimal gland tissue, containing delphinidin-3,5-diglucoside as an active substance.

14. Inhibitor to the generation of radical oxygen in the lacrimal gland tissue, containing the maqui berry extract including delphinidin-3, 5-diglucocide as an active substance.

MODES FOR CARRYING OUT THE INVENTION

Figure 1:
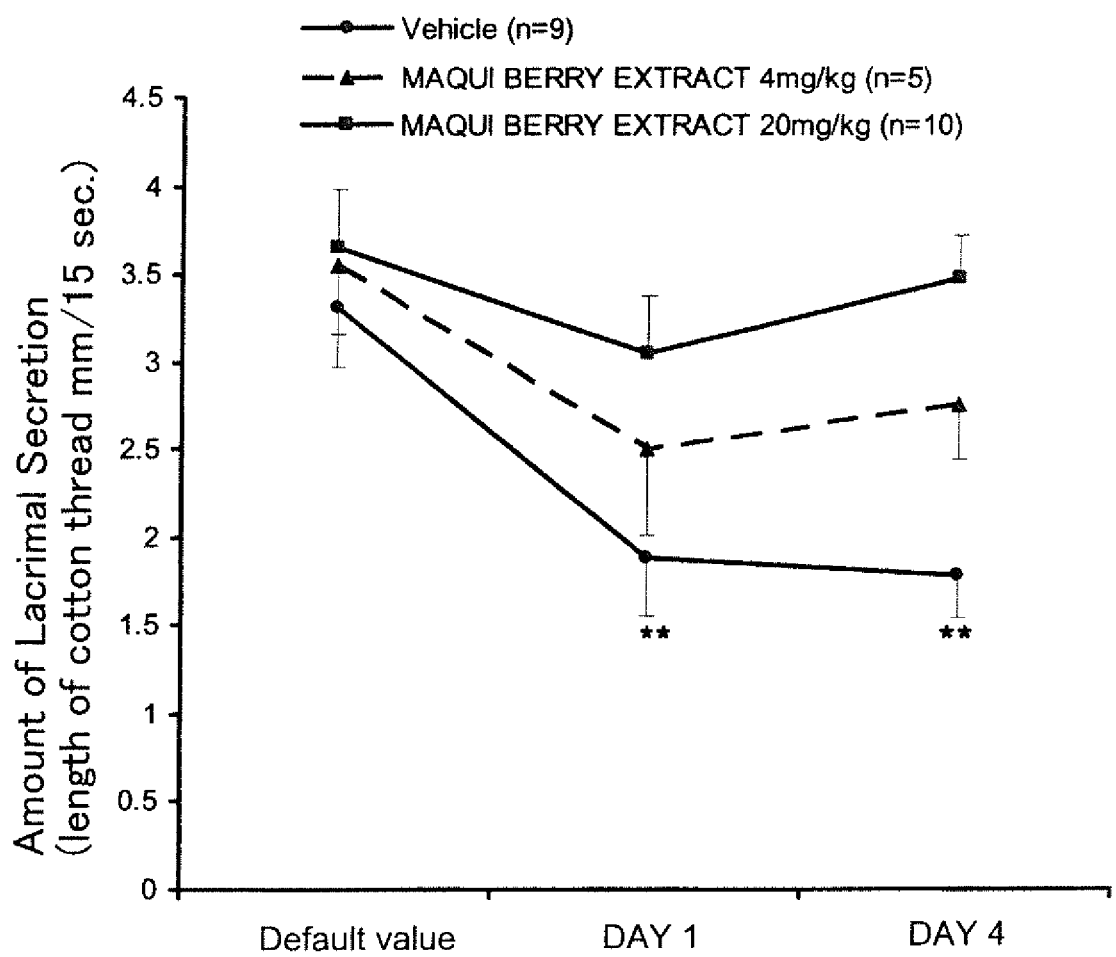
FIG. 1 is a graph showing changes in the lacrimal secretory ability after four consecutive-day administrations of maqui berry extract to mice suffering from stress-induced dry eye, (indicated by the measured value, average plus-or-minus standard error, **$p<0.01$ to default value, #$p<0.05$ to vehicle).

Hereinafter, the invention is described in detail.

Regarding this invention, the prophylactic and therapeutic agent for dry eye, an inhibitor to the deterioration of the lacrimal secretory ability or an inhibitor to the generation of radical oxygen in lacrimal gland tissue, contains an active substance that is maqui berry extract or delphinidin glycoside extracted from the maqui berry.

Also, the prophylactic and therapeutic agent for dry eye, an inhibitor to the generation of radical oxygen in lacrimal gland tissue, contains as an active substance either one or more of delphinidin-3-sambubioside-5-glucoside, delphinidin-3,5-diglucoside, delphinidin-3-sambubioside and delphinidin-3-glucoside.

The aforementioned delphinidin is a chemical compound, as described in the following formula (1).

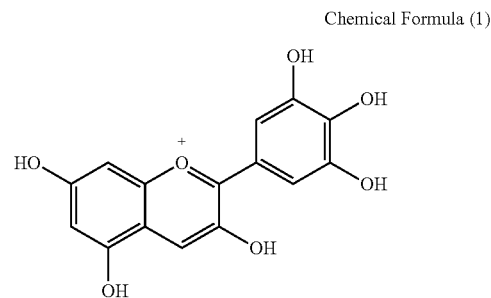

Chemical Formula (1)

Delphinidin is a type of anthocyanidin and antioxidant that is known as a major plant pigment. Also, anthocyanidin, as aglycon, is linked to sugar or a sugar chain to form anthocyanin (glycoside).

Although the method for obtaining delphinidin is unlimited, it is possible to use either a plant-derived substance or a chemically synthesized one. It is possible of course to use a substance that is commercially available (i.e. extrasynthese).

Delphinidin glycoside, as used in this invention, is for example described in the following chemical formula (2).

Chemical Formula (2)

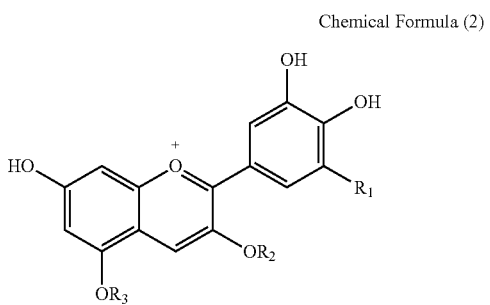

(R1 to R3 are replaced by hydroxyl sugar (saccharide) monomer, or dimer.)

Although the above-referenced delphinidin glycoside is not limited to that specific substance for example, it is preferably limited to delphinidin-3-sambubioside-5-glucoside, delphinidin-3,5-diglucoside, delphinidin-3-sambubioside and delphinidin-3-glucoside. These chemical compounds are the ones in which the descriptions are replaced by R1 to R3 of the compounds shown in the above chemical formula 2. It is possible also to use one or more than one.

CHART 1

|  | $R_1$ | $R_2$ | $R_3$ |
|---|---|---|---|
| Delphinidin 3-O-sambubioside-5-O-glucoside | OH | Sam | Glu |
| Delphinidin 3,5-O-diglucoside | OH | Glu | Glu |
| Delphinidin 3-O-sambubioside | OH | Sam | H |
| Delphinidin 3-O-glucoside | OH | Glu | H |

Glu: glucose,
Sam: sambubiose

The method in obtaining delphinidin glycoside is not especially limited. It is possible to use either a plant-derived substance or a chemically synthesized one. In the case that the delphinidin glycoside is extracted from a plant besides the maqui berry, it is possible to use bilberry, cassis, cranberry, Concord (grape), pomegranate or the like as an ingredient. However, maqui berry extract is preferred, since the maqui berry contains a high concentration of delphinidun glycoside that is the active substance of this invention, and it is easily extracted. It is also possible to use a substance that is commercially available.

The maqui berry (also known as *Aristotelia Chilensis*) is a berry plant native to the southern part of Chili in South America. Its antioxidant action is known to be extremely strong.

The maqui berry is also known to contain delphinidin glucoside or deliphinidin-3-sambubioside-5-glucoside and delphinidin-3,5-O-diglucoside, which substances are not contained in other berries such as bilberry and cassis (aka. blackcurrant).

Research conducted by the inventors of this invention confirmed that the maqui berry also contains delphinidin-3-sambubioside and delphinidin-3-glucoside as well as the above mentioned delphinidin-3-sambubioside-5-glucoside and delphinidin-3,5-diglucoside of delphinidin glucoside. Delphinidin-3,5-digluoside especially is an excellently active substance and thus efficiently works as a prophylactic and therapeutic agent for dry eye, as an inhibitor to deterioration of the lacrimal secretory ability, or as an inhibitor to the generation of radical oxygen in the lacrimal gland tissue.

The content of delphinidin glycoside of the above maqui berry extract is not especially limited. However, it is preferable that when the maqui berry extract is 100 wt %, then 6-25 wt % should contain delphinidin-3,5-O-diglucoside, preferably 10-20 wt %, and that 1-10 wt % should contain delphinidin-3-sambubioside-5-glucoside, preferably 4-8 wt %.

Of this invention, no particular portion of the maqui berry plant is limited in extracting the delphinidin glycoside as an active substance. The fruit, the seeds, the flower, the leaves, stems or the like can be used. Yet, the fruit is preferable, since it is possible to extract a high concentration of the above active substance from the fruit.

As an extracting solvent, it is possible to use a polar solvent such as water, methanol, ethanol, isopropyl alcohol, 1,3-butylene glycol, ethylene glycol, propylene glycol, glycerin, ethyl acetate or the like. It is also possible to mix two or more solvents from among the above solvents. Water ethanol or its mixture, hydrous ethanol, is preferred as an extracting solvent for efficiently extracting the active substance.

In the case that water is used as an extracting solvent, the type of water is not limited. Tap water, distilled water, alkaline-ion water, deep water or the like can be used.

The amount of concentration of ethanol is not particularly limited in the case that hydrous ethanol is used as an extracting solvent. However, the concentration of ethanol should be 10-90% (wt/wt), preferably 20-80% (wt/wt). The reason that the concentration of ethanol is less than 90% (wt/wt), as above, is that too high a concentration of ethanol makes the oil content of the maqui berry easily dissolve into hydrous ethanol.

The extracting temperature should be 20~80 degrees Celsius, preferably 40~50 degrees Celsius. If the extracting temperature is too low, the active substance is not easily extracted. If it is to high, the active substance is degraded, thus the physiological activity (health functioning ability) is lessened.

Methods of extraction, for example, include continuous extraction, soaking extraction, countercurrent extraction, or one that can be used with any optional equipment at room temperature or by heating under reflux.

As for the specific method of extracting, put the extraction ingredient (i.e. the maqui berry fruit or the like) into the processing vat filled with an extracting solvent and stir until the active substance of the extraction ingredient seeps into the solvent. If using hydrous ethanol for example as the extracting solvent, the extraction is conducted by the solvent being approximately two to 100 times as much weight as the extraction ingredient, from 30 minutes duration to two hours. After the active substance has seeped into the solvent, then filter the solvent and remove the residue to obtain the extracted liquid.

Afterward, according to the ordinary method, apply the dilution, concentration, refining or drying method or the like to the extracted liquid to obtain the prophylactic and therapeutic agent for dry eye or the inhibitor to deterioration of the lacrimal secretory ability.

The refining method is conducted by absorbing the extracted liquid that is filtered through the synthetic absorption resin or gel filtration resin or the like and then eluting the extracted liquid in methanol, ethanol or the like to concentrate it.

The prophylactic and therapeutic agent for dry eye or the inhibitor to deterioration of the lacrimal secretory ability of this invention can be used as an ingredient of any food and drink such as confectionary (chewing gum, candies, caramels, chocolates, cookies, jellies, gummies, tablet shaped sweets or other snack food), noodles (Japanese buckwheat noodles called Soba, Japanese wheat noodles called Udon, Chinese noodles called Ramen or the like), dairy food (milk, ice cream, yogurt, or the like), seasoning (fermented bean paste called Miso, soy sauce called Shoyu or the like), soups, drinks (juice, coffee, black tea, green tea, carbonated drinks, sports supplement drinks or the like) and general foods and healthy foods (tablet type, capsule type or the like), and nutritional supplements (nutritious supplement drink or the like). The prophylactic and therapeutic agent for dry eye or the inhibitor to deterioration of the lacrimal secretory ability of this invention can be applied to the above foods and drinks.

According to the above types of foods and drinks, the following ingredients can be added: Glucose, fructose, sucrose, maltose, sorbitol, stevioside, corn syrup, lactose, citric acid, tartaric acid, malic acid, saccinic acid, lactic acid, L-ascorbic acid, dl-α-tocopherol, sodium erythorbate, glycerin, propylene glycol, glycerin fatty acid ester, polyglycerol fatty acid ester, sucrose fatty acid ester, sorbitan fatty acid ester, propylene glycol fatty acid ester, Arabian gum, carrageenan, casein, gelatin, pectine, agar-agar (gelatin made from seaweed), vitamin B series, nicotinic-acid amide, pantothenate acid calcium, amino acids, calcium salts, pigment, aroma chemicals, preservatives or the like.

The specific method of extracting is herein described. Firstly, spray-dry or freeze-dry the prophylactic and therapeutic agent for dry eye with powdered cellulose to make it a powder, a granule, a tablet or liquid to easily use with different kinds of food and drinks (ready-to eat meals or the like). Also, it is possible to dissolve the prophylactic and therapeutic agent for dry eye for example in oil and fat, in ethanol, in glycerin or in a mixture of these substances to use such a liquid for making dry food or drinks. Also, it is possible to make the extract into a powder or granule by mixing it with a binder such as Arabian gum, dextrin or the like to add to dry food or drinks.

The total amount of the active substance of the prophylactic and therapeutic agent for dry eye or inhibitor to deterioration of the lacrimal secretory ability of this invention, which can also be added to food and drinks, is preferably 1 to 20 wt % or less, since the main objective of this invention is health maintenance.

The prophylactic and therapeutic agent for dry eye or inhibitor to deterioration of the lacrimal secretory ability of this invention can be used as the raw material for medicines (including drugs and quasi-drugs). In the making of drugs, the prophylactic and therapeutic agent for dry eye of this invention can be appropriately mixed with raw materials such as, for example, vehicles (glucose, sucrose, white soft sugar, sodium chloride, starch, calcium carbonate, kaolin, crystalline cellulose, cacao oil, hydrogenated vegetable oil, talc or the like), binders (distilled water, normal saline solution, ethanol in water, ethanolic solution, simple syrup, dextrose in water, starch solution, gelatin solution, carboxymethyl cellulose, potassium phosphate, polyvinyl pyrrolidone or the like), disintegrating agents (alginate sodium, agar-agar, sodium hydrogen carbonate, sodium lauryl sulphate, stearic acid monoglyceride, starch, lactose, powdered aracia, gelatin, ethanol or the like), suppressive agents for disintegration (white soft sugar, stearin, cacao oil, hydrogenated oil or the like), for absorption promoters (quaternary ammonium base, sodium lauryl sulphate or the like), for absorbents (glycerin, starch, lactose, kaolin, bentonite, silic acid or the like), or for lubricant agents (purified talc, stearate, polyethyleneglycol or the like.

The prophylactic and therapeutic agent for dry eye or inhibitor to deterioration of the lacrimal secretory ability of this invention can be orally administered in the form of tablets, pills, soft or hard capsules, subtle granules, powders, granules, liquids or the like. However, the therapeutic agent can also be parenterally administered in different forms of solution or together with a dispersant, a suspending agent, a stabilizer or the like by direct administration into the local tissue by intradermal injection, by hypodermic injection, by intramuscular injection or by intravenous injection or the like. The therapeutic agent can also be used as a suppository eye drop.

The applied dose can be adjusted according to the method of administration or to the condition of the disease or to the age of the patient or the like. Adults can normally take approximately 0.5 to 5000 mg of the active substance per day, while children can take 0.5 to 3000 mg per day. The compounding ratio of the prophylactic and therapeutic agent for dry eye or inhibitor to deterioration of the lacrimal secretory ability of this invention can be adjusted according to the mode of administration. When the dietetic composition is orally or mucosally administered, the applied dose preferably is 0.3 to 15.0 wt %. When the dietetic composition is parenterally administered, the dose preferably is 0.01 to 10 wt %. The dose varies depending on the condition of the patient, so that a dose less than the above amount may be sufficient, or a greater amount may sometimes be needed.

Working Example

Examples of this invention are described herein, which verify the actions, effects or the like of the prophylactic and therapeutic agent for dry eye, of the inhibitor to deterioration of the lacrimal secretory ability, and of the inhibitor to the generation of radical oxygen in the lacrimal gland tissue, which show that the scope of this invention is not limited to its products and manufacturing methods.

Working Example 1: Preparation of the Maqui Berry Extract

Maqui berry (*Aristotelia Chilensis*) fruit in distilled water was stirred at 50 degrees Celsius to obtain the extract liquid. After that, the liquid was filtered and passed through a synthetic-absorbent column chromatography, and then the maqui berry extract liquid containing the active substance was eluted in an aqueous solution of 80% ethanol. Then, the maqui berry extract liquid was dried into the maqui berry extract (Working Example 1). Analyzing the maqui berry extract of Working Example 1 by HPLC, the extract was identified to contain delphinidin 3,5-diglucoside of 12.26% and delphinidin 3-sambubioside-5-glucoside of 7.76%.

Working Examples 2 to 5: Isolating the Related Ingredients of the Maqui Berry Extract In the past, it was identified that the maqui berry extract showed curative action on mice models having dry eye. To find the active substance of the extract, anthocyanin was isolated from the maqui berry and refined.

As for the method of isolating and refining, the maqui berry extract (0.25 g/5 ml) obtained by the preparation described in Working Example 1 was filtered through a cotton plug and then passed through an ODS Sep-Pak (Waters Corporation). Then, the extract was isolated and refined by HPLC for sampling. The condition is as follows.

Mobile phase: 25% MeOH 0.3% TFA
UV: 520 nm
Flow rate: 9.0 ml/min
Column: Inertsil PREP-ODS 20×250 mm The following facts were confirmed in isolating and refining the maqui berry extract.

Delphinidin-3sambubioside-5-glucoside (Fr. 1: Working Example 2) 6.3 mg isolated Delphinidin-3,5-diglucoside (Fr. 2: Working Example 3) 6.3 mg isolated Delphinidin-3-sambubioside (Fr. 5: Working Example 4) 2.5 mg isolated Delphinidin-3-glucoside (Fr. 6: Working Example 5) 4.8 mg isolated Each example is 95% pure or more.

The HPLC test results are shown in FIGS. 7 to 11.

Test Example 1: Evaluation of the Inhibitory Action to Deterioration of the Lacrimal Secretory Ability on Mice Having Symptoms of Dry Eye Test Condition Regarding the maqui berry extract (Working Example 1), the evaluation on the inhibitory action to deterioration of the lacrimal secretory ability on mice having symptoms of stress-induced dry eye was done according to the following steps.

As a test animal, C57/B female mice of 10 weeks old were used. There were 5-10 mice per group.

The procedure for deteriorating the lacrimal secretory ability (stress loading test) was done according to the document by: (Tracy L. Bale, Angelo Contarino, George W. Smith, Raymond Chan, Lisa H. Gold, Paul E. Sawchenko: Mice deficient of corticotropin-releasing hormone receptor-2 display anxiety-like behavior and are hypersensitive to stress. Nature Genetics. 24: 410-414, 2000.) In other words, the mice were held in polypropylene-centrifuge tubes (content capacity: approx. 60 mL for four hours a day, and they had room to breathe and egest. During the time that the mice were restrained in the tube, wind was blown into the faces of the mice at a speed of 0.5 to 1.0 m/s. During the off-operation period in the four hours, the mice were free to eat and drink water in the cage. The above procedure was done repeatedly during the period of administering the maqui berry extract.

The maqui berry extract (Working Example 1), appropriately eluted in distilled water, was administrated to the mice by oral sonde under the following conditions.

Content amount: 4 mg/kg, 20 mg/kg
Control solution: Distilled water (vehicle)
Number of tests: once a day for four or eight consecutive days The condition of restraint is as follows:
Temperature: 23.5° C.
Humidity: 70±15%
Lighting hours: 8:00 to 20:00. Cut-off hours: 20:00 to 8:00
Food and water: Solid food and tap water, discretionally taken The amount of lacrimal secretion was measured in the following way.

Cotton thread ("ZONE-QUICK" by the Showa Yakuhin Kakou Co., Ltd.) was inserted into the right and left external canthus of the mice for 15 seconds. The length of brownish discoloration on the cotton thread that was penetrated by the lacrimal liquid was measured to an accuracy of 0.5 mm. The measurements were taken before the stress-loading period (default value) of the administration, again on the following day during the stress-loading period, and again before the stress-loading period. The average value of both eyes of the mice should be the amount of lacrimal secretion for each mouse.

The statistics analysis was done according to the following method.

A paired t-test was done to compare the default value to the value on the fourth day of administration. Many unpaired t-tests or Dunnett's tests were done in comparing the groups.

Result and Effect of Test Example 1

Figure 2:
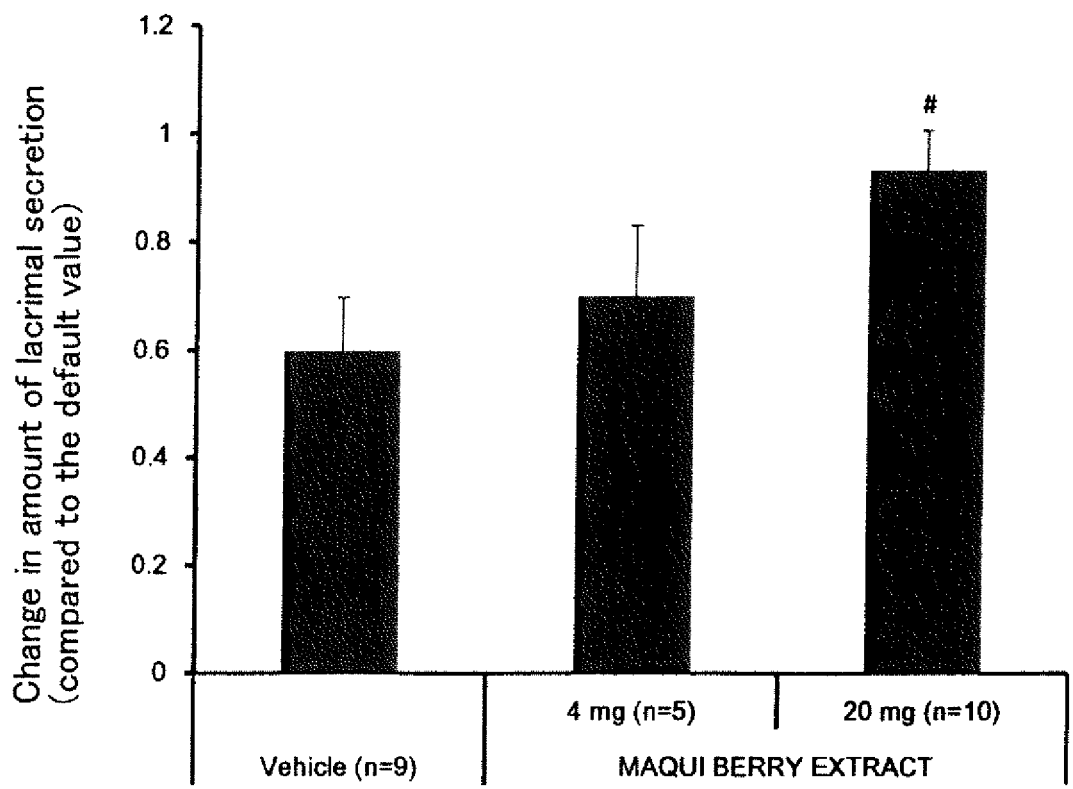
FIG. 2 is a graph showing changes in the lacrimal secretory ability after four consecutive-day administrations of maqui berry extract to mice suffering from stress-induced dry eye, (indicated by the value of the variable compared to the value before administration, average plus-or-minus standard error, **$p<0.01$ to default value, #$p<0.05$ to vehicle).

(A) Result of the Four-Day Repeated Administration (FIG. 1 or FIG. 2)

FIG. 1 shows the result in the changes (measured value) of the lacrimal secretory ability after administering the maqui berry extract to the mice having symptoms of stress-induced dry eye. The amount of lacrimal liquid shows a decreasing trend of the maqui berry-extract administered group and the vehicle-administered group. Especially of the vehicle-administered group, the values on the first day of administration and on the fourth day decreased significantly, compared to the default value.

FIG. 2 shows the change in ratio compared to the pre-administration value (default value). As shown in FIG. 2, the change in ratio of the fourth day of administration compared to the default value shows a significantly small change in the 20 mg/kg maqui berry-extract administered group compared to the vehicle-administered group. Therefore, it was verified that the maqui berry extract of this example has the action to inhibit deterioration of the lacrimal secretory ability, thus making it effective as a prophylactic and therapeutic agent for dry eye.

Figure 3:
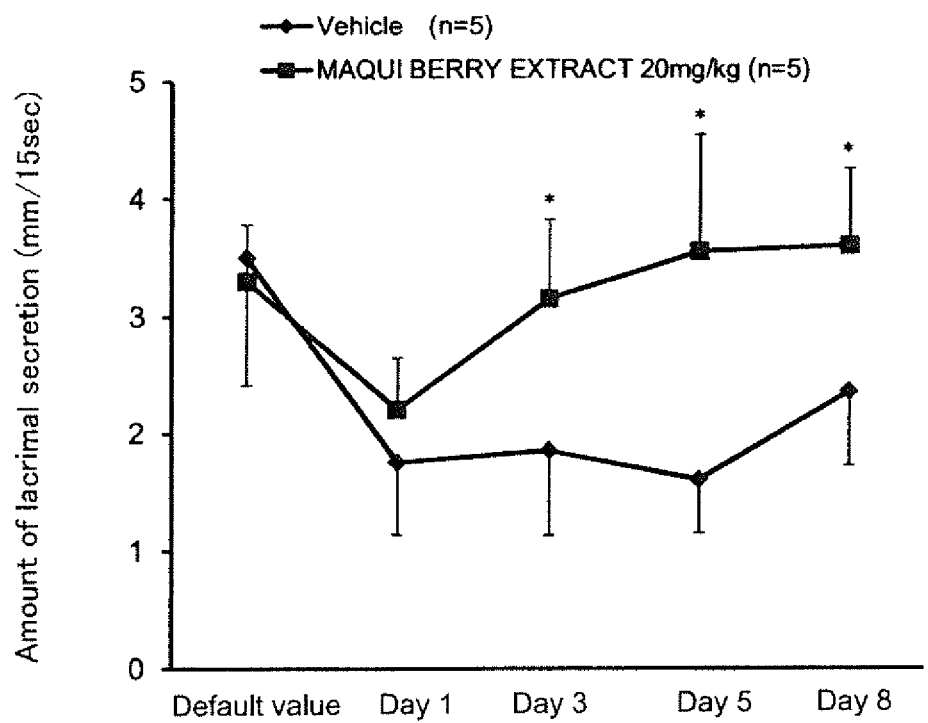
FIG. 3 is a graph showing changes in the lacrimal secretory ability after four consecutive-day administrations of maqui berry extract to mice suffering from stress-induced dry eye.

(B) Result of the Eight-Day Repeated Administration (FIG. 3)

FIG. 3 shows the result in the changes (measured value) of the lacrimal secretory ability after administering the maqui berry extract to the mice having symptoms of stress-induced dry eye. As shown in FIG. 3, the amount of lacrimal secretion of the 20 mg/kg maqui berry-extract administered group was significantly larger than that of the vehicle-administered group.

Therefore, it was verified that the maqui berry extract of this example has the action to inhibit deterioration of the lacrimal secretory ability, thus making it effective as a prophylactic and therapeutic agent for dry eye.

Test Example 2: Evaluation 1 on the Inhibitory Action of Maqui Berry Extract to Radical Oxygen Species, Using Isolated Lacrimal Glands of Mice (2-1) Test Condition The action of the maqui berry extract to radical oxygen species in lacrimal gland tissue was evaluated using mice in vivo model.

The maqui berry extract (Working Example 1), appropriately eluted in distilled water, was administrated to the mice by oral sonde under the following condition.

Animal: C57BL6, female, 10 weeks old
Content amount: 4 mg/kg, 20 mg/kg
Control solution: Distilled water (vehicle)
Number of tests: once a day for eight consecutive days
Number of samples: 5 to 10 mice per group
The restraint conditions of the mice were as follows:
Temperature: 23±5° C.

Humidity: 70±15%

Lighting hours: 8:00 to 20:00. Cut-off hours: 20:00 to 8:00

Food and water: Solid food and tap water, discretionally taken

The evaluation of the inhibitory action to radical oxygen species was done in the following way.

An isolated lacrimal gland was placed in a test tube, and 25 mg tissue/mL of cold phosphate-buffered saline (PBS) was added. After that, zirconia beads were added to the lacrimal gland that is to be crushed by a bead grinder. Then, 50 µL each of cell suspension was dispensed. Then, the maqui berry extract of Working Example 1 (1, 10 µg/mL) was added to the cell suspension, and then DCFH-DA solution as the radical oxygen series was added to make the final level of concentration at 75 µM. Then, after 60 minutes of incubation at 37 degrees Celsius, the cells were washed in PBS. The fluorescence-plate reader measured the intensity of fluorescence at (λ485/528).

Figure 4:
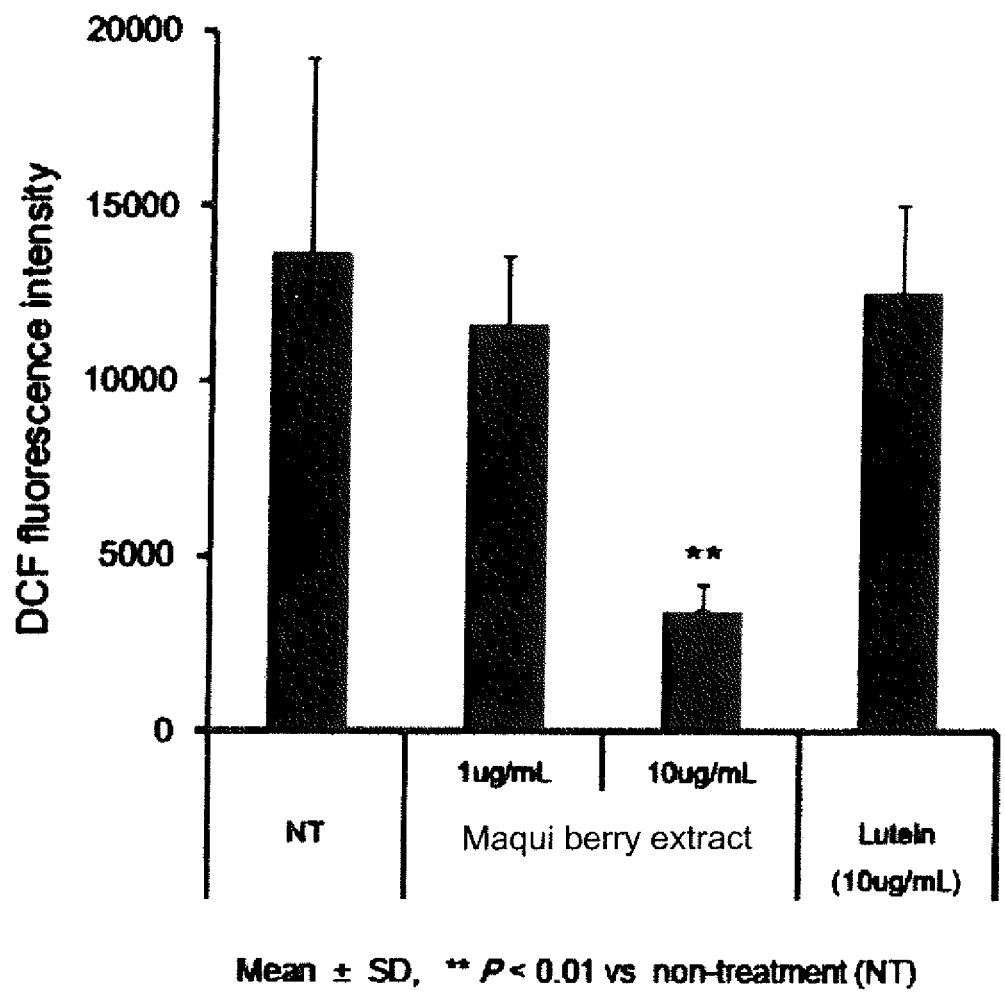
FIG. 4 is a graph showing the effect of maqui berry extract in inhibiting the generation of radical oxygen species in lacrimal cells.

As a Comparative Example, the same test was done on lutein 10 µg/mL (compare and contrast). FIG. 4 shows the results.

Figure 5:
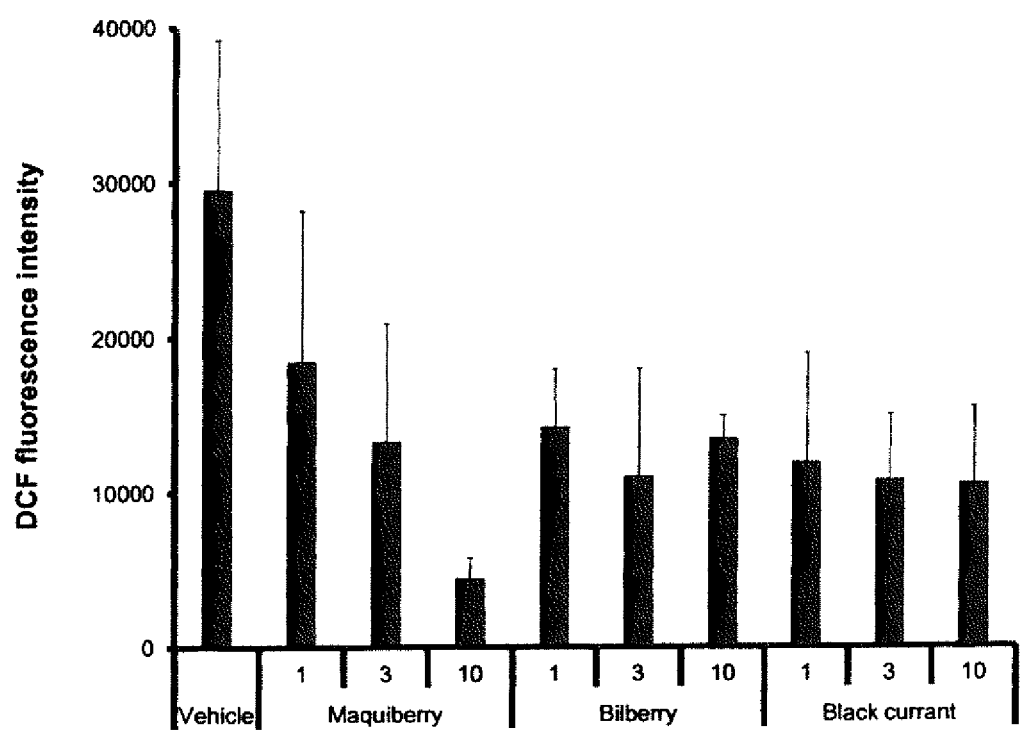
FIG. 5 is a graph comparing the effect of maqui berry extract and other extracts in inhibiting the generation of radical oxygen species in lacrimal cells.

Also, as a Comparative Example, the same test was done on the bilberry extract (Indena) and on the black currant extract (Tama Biochemical Co., Ltd.). FIG. 5 shows the results.

Furthermore, the same tests were done on the following examples.

Fr. 1: delphinidin-3-sambubioside-5-glucoside (Working Example 2)

Fr. 2: delphinidin-3, 5-glucoside (Working Example 3)

Fr. 5: delphinidin-3-sambubioside (Working Example 4)

Fr. 6: delphinidin-3-glucoside (Working Example 5)

Figure 6:
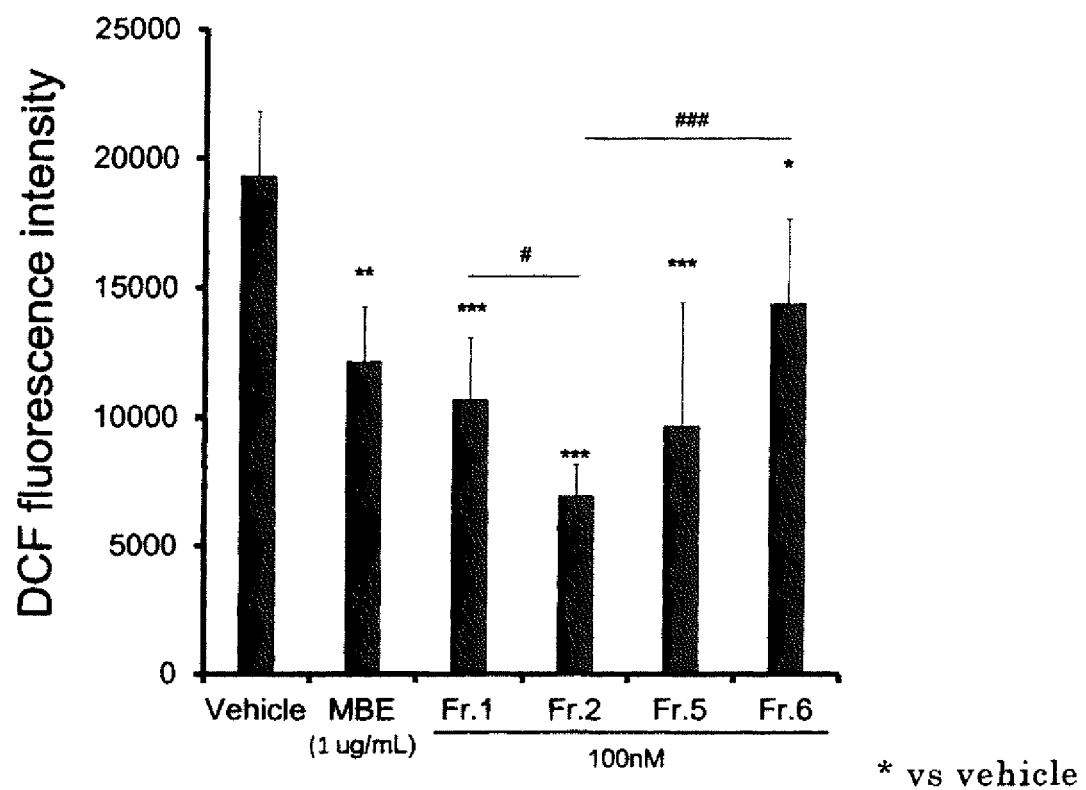
FIG. 6 is a graph showing the effect of delphinidin glycoside, isolated from maqui berry extract, in inhibiting the generation of radical oxygen species.
Figure 7:
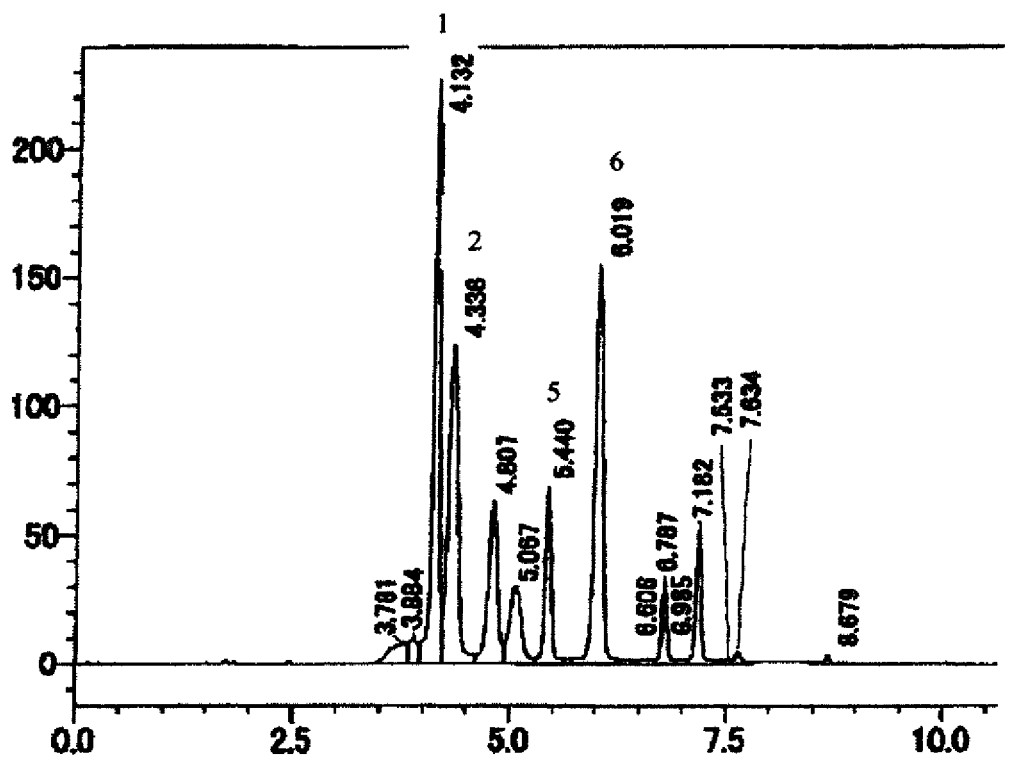
FIG. 7 is a high-performance liquid chromatography (HPLC) chart of the maqui berry extract.
Figure 8:
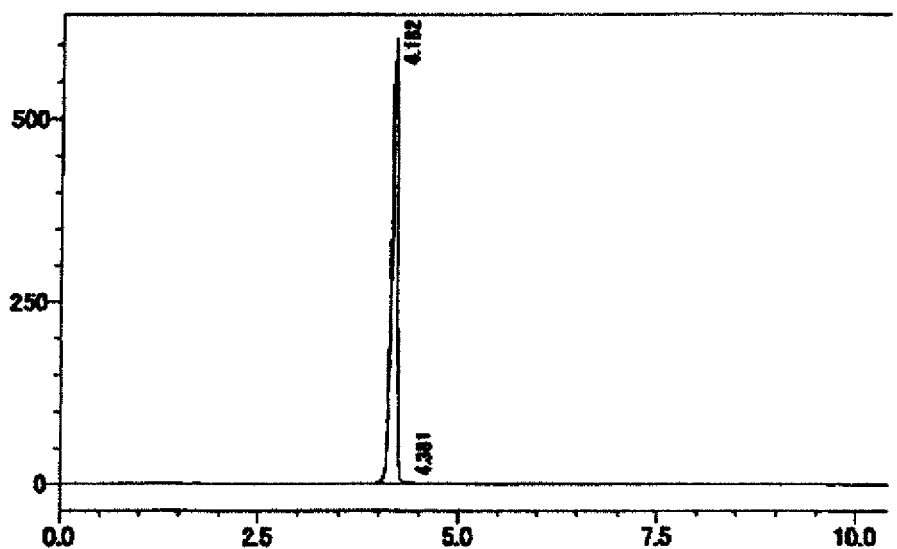
FIG. 8 is an HPLC chart of the maqui berry extract Fr. 1: delphinidin-3-sambubioside-5-glucoside.
Figure 9:
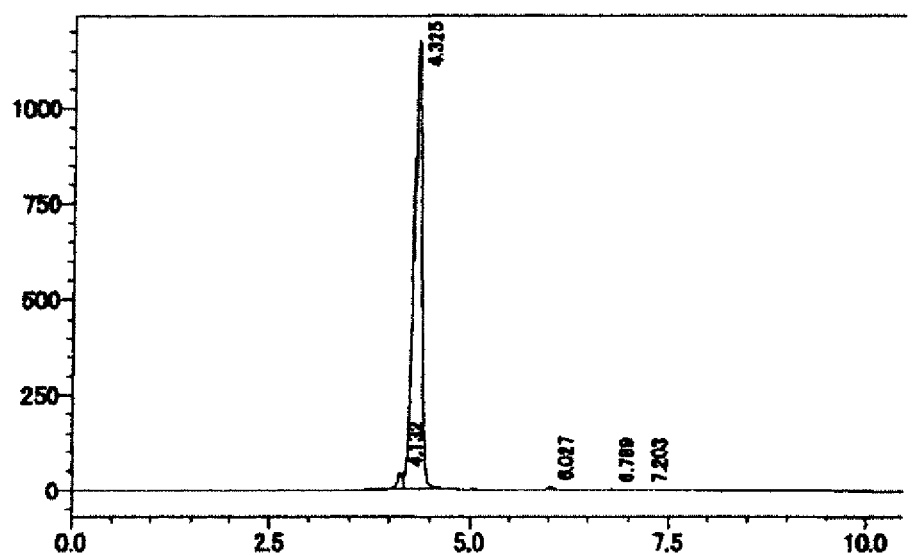
FIG. 9 is an HPLC chart of the maqui berry extract Fr. 2: delphinidin-3, 5-glucoside.
Figure 10:
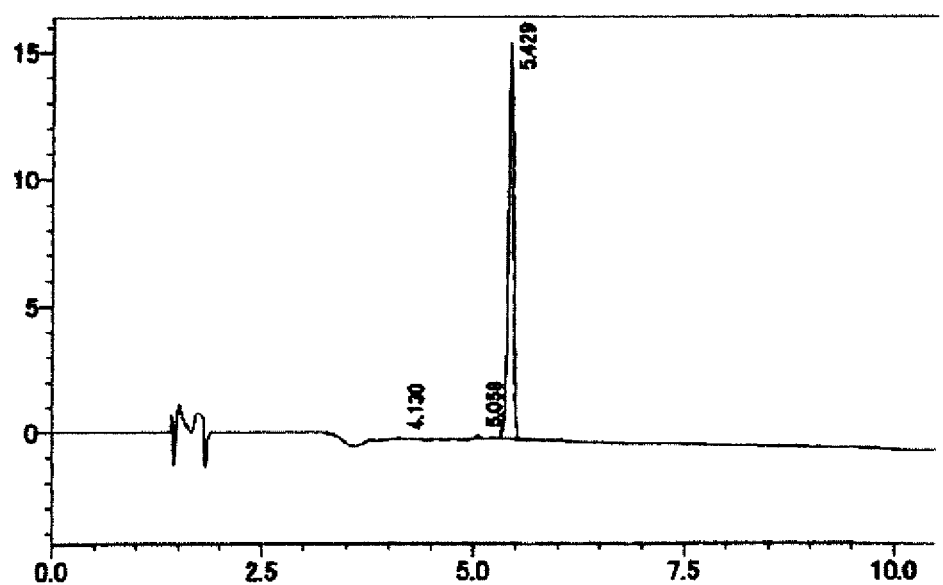
FIG. 10 is an HPLC chart of the maqui berry extract Fr. 5: delphinidin-3-sambubioside.
Figure 11:
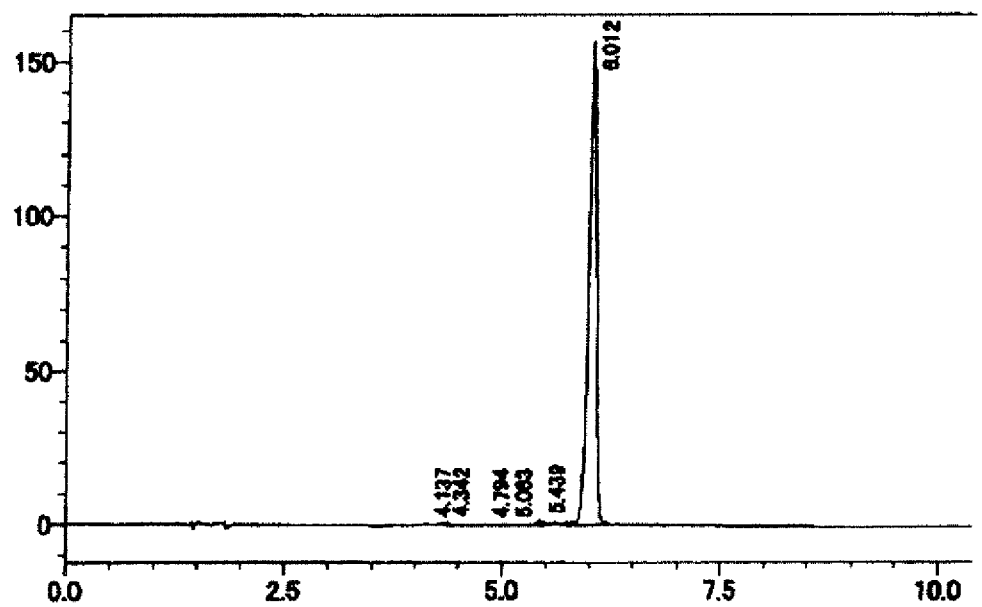
FIG. 11 is an HPLC chart of the maqui berry extract Fr. 6: delphinidin-3-glucoside.

FIG. 6 shows the results.

(2-2) Result and Effects of Test Example 2

As shown in FIG. 4, the maqui berry extract (10 µg/mL) significantly inhibited the radical oxygen series in lacrimal gland tissue. It was verified that compared even to lutein that is known for its antioxidant action in effectively preventing ophthalmopathy, the maqui berry extract has an excellent effect in inhibiting radical oxygen in lacrimal gland tissue.

As shown in FIG. 5, compared to the bilberry extract and cassis extract (black currant), the maqui berry extract significantly inhibited the radical oxygen. Therefore, it was verified that the maqui berry extract is effective as a prophylactic and therapeutic agent for dry eye and has an excellent effect as a prophylactic and therapeutic agent for dry eye compared to other ingredients. In FIG. 5, "1" and "3" and "10" show the additive amount µg/mL of each botanical extract, and "maqui berry" is the maqui berry extract of Working Example 1.

As shown in FIG. 6, the radical oxygen was significantly inhibited in Fr. 1: delphinidin-3-sambubioside-5-glucoside (Working Example 2), Fr. 2: delphinidin-3,5-glucoside (Working Example 3), Fr. 5: delphinidin-3-sambubioside (Working Example 4) and Fr. 6: delphinidin-3-glucoside (Working Example 5). Thus, it was verified that the above substances contained in the maqui berry extract are involved in effectively preventing and treating dry eye.

Test Example 3: Evaluation 2 of the Inhibitory Action Against Radical Oxygen Species of the Maqui Berry Extract Using Isolated Lacrimal Glands of Mice

(3-1) Test Condition

Figure 12:
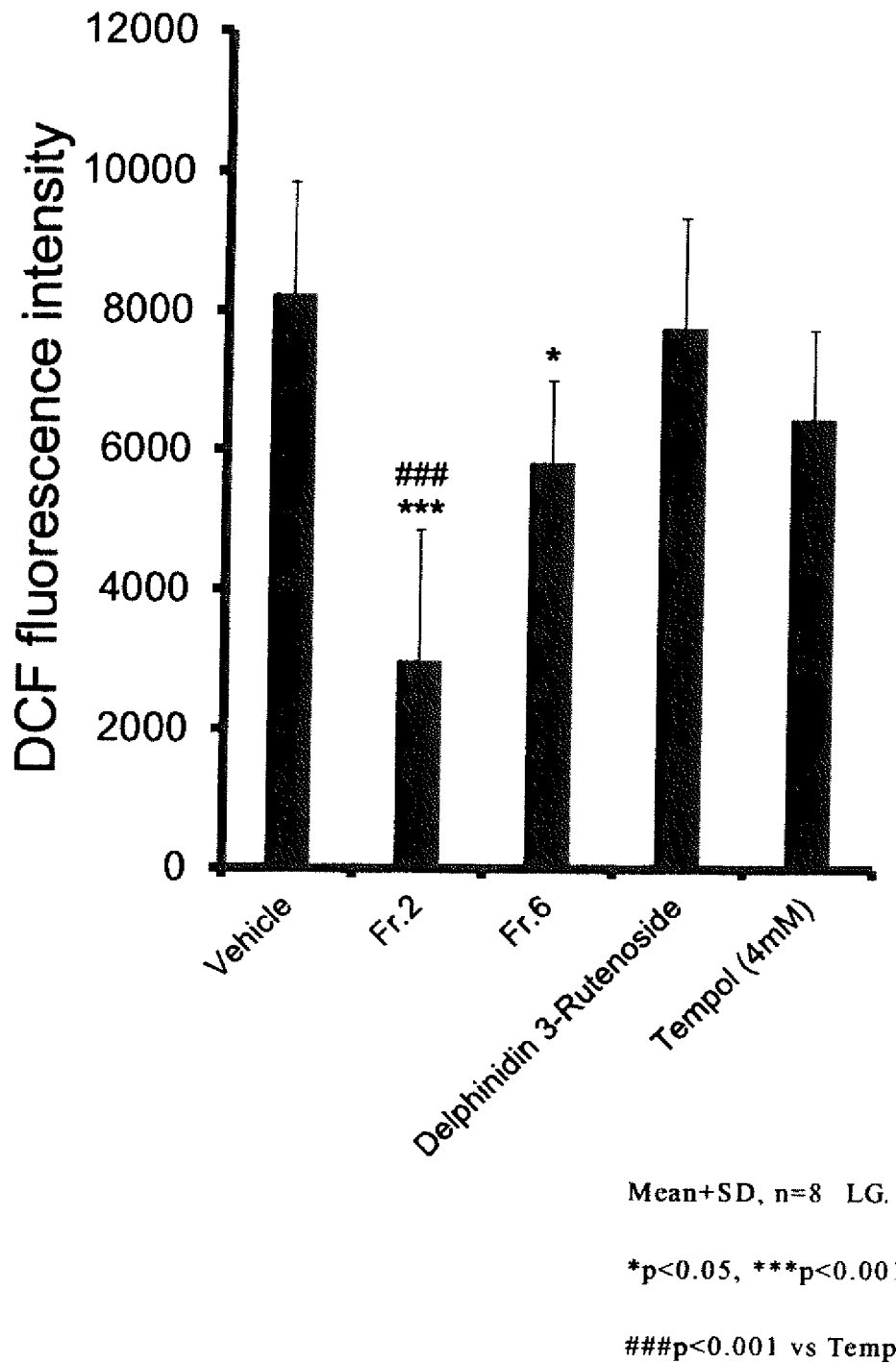
FIG. 12 is a graph showing the comparative effect of Fr. 2: delphinidin-3,5-glucoside (Working Example 3), Fr. 6: delphinidin-3-glucoside (Working Example 5) and delphinidin 3-rutinoside in inhibiting the generation of radical oxygen species in lacrimal cells.

Regarding Fr. 2: delphinidin-3,5-diglucoside (Working Example 3), Fr. 6: delphinidin-3-glucoside (Working Example 5) and delphinidin-3-rutinoside (Comparative Example 1: substance contained in cassis), the same evaluation as in Test Example 2 was done. FIG. 12 shows the results.

Figure 13:
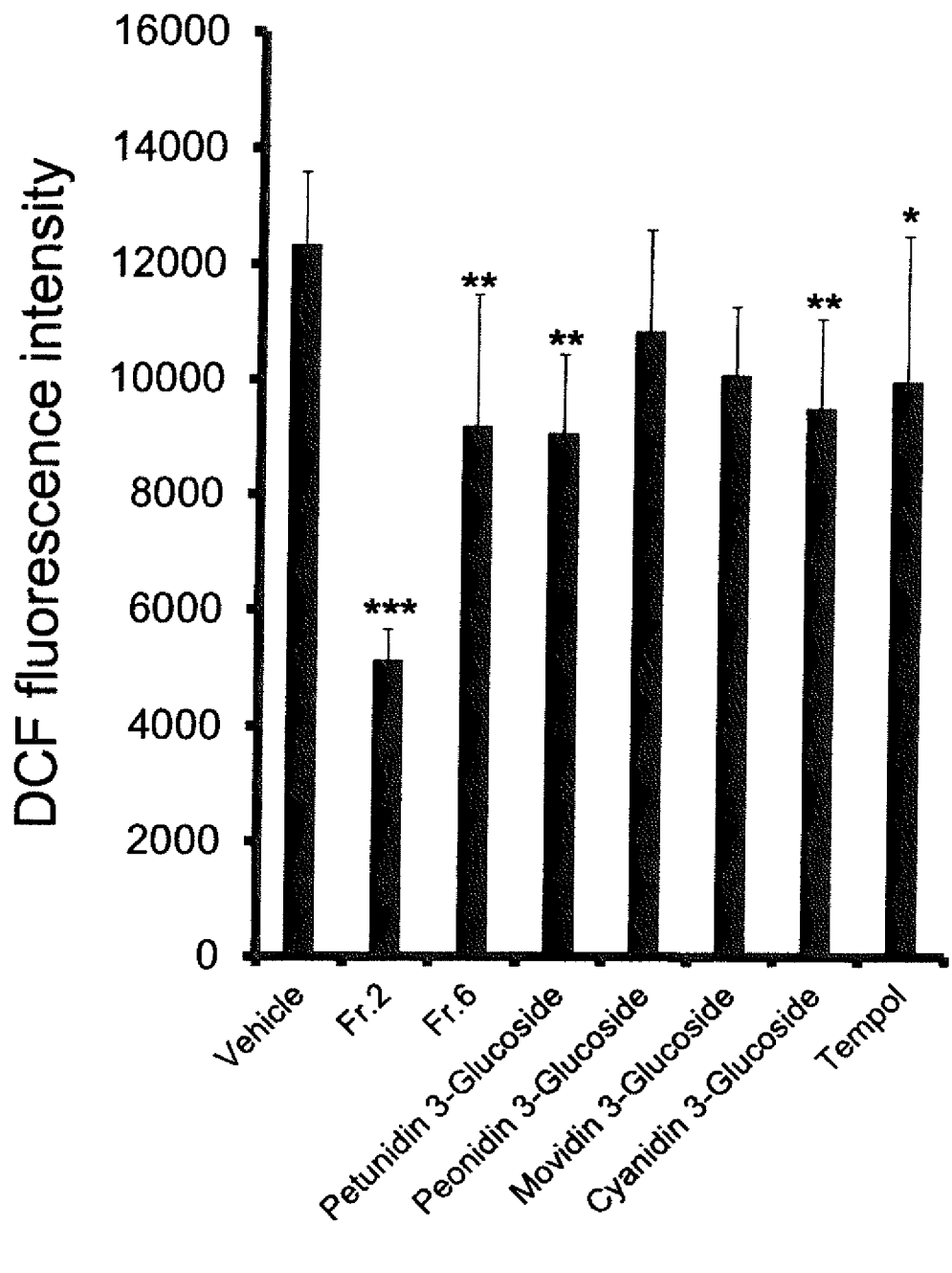
FIG. 13 is a graph showing the comparative effect of Fr. 6: delphinidin-3-glucoside (Working Example 5) and other anthocyanins (i.e. petunidin-3-glucoside, peonidin-3-glucoside, movidin-3-glucoside, cyaniding-3-glucoside) in inhibiting the generation of radical oxygen species in lacrimal cells.

Regarding Fr. 6 delphinidin-3-glucoside (Working Example 5) and the other anthocyanin series (petunidin-3-glucoside, peonidin-3-glucoside, malvidin-3-glucoside and cyaniding-3-glucoside), the evaluation of Test Example 2 was done. FIG. 13 shows the results.

(3-2) Test Result and Effect of the Working Example of Test Example 3

As shown in FIG. 12, delphinidin-3-rutinoside (Comparative Example 1) did not inhibit radical oxygen. Instead, Fr. 2: delphinidin-3,5-diglucoside (Working Example 3) and Fr. 6: delphinidin-3-glucoside (Working Example 5) inhibited radical oxygen, especially Fr. 2: delphinidin-3,5-diglucoside (Working Example 3), which is the particular substance of the maqui berry that shows excellent inhibitory action against radical oxygen species.

Thus, compared to other delphinidin glycosides, it was verified that Fr. 2: delphinidin-3,5-diglucoside (WorkingExample 3), which is the particular substance of the maqui berry, excellently effectively prevents and treats dry eye.

Also, as shown in FIG. 13, compared to other anthocyanins, Fr. 2: delphinidin-3,5-diglucoside (Working Example 3), which is the particular substance of the maqui berry, showed especially excellent action in inhibiting radical oxygen in lacrimal cells.

Test Example 4: Absorption Test, Concerning the Lacrimal Cells, on the Substance Contained in the Maqui Berry Extract

(4-1) Objective of the Test

Test Example 1 identified that the maqui berry extract effectively inhibits dry eye and obviously has a stronger inhibitory action than that of bilberry and cassis. Also, in terms of the substance, delphinidin-3,5-diglucoside (Working Example 3), which is the particular anthocyanin of the maqui berry, showed a stronger inhibitory action than that of other anthocyanins, i.e. of delphinidin-3-glucoside (the main anthocyanin contained in bilberry) and of delphinidin-3-rutinoside (the main anthocyanin contained in cassis: Comparative Example 1). This test was done to compare the intake amount of the anthocyanin into the lacrimal cells using the HPLC to identify the mechanism of actions. This test was done to compare the amount of absorption of anthocyanin by the lacrimal cells, using HPLC to identify the mechanism of the actions.

(4-2) Test Condition

The test was done in the following way. Each anthocyanin (of delphinidin-3,5-diglucoside, delphinidin-3-O-glucoside and delphinidin-3-Orutinoside) was added to the lachrymal-cells suspension at the final concentration of 100 µM.

After that, the suspension was incubated for 30 minutes at 37 degrees Celsius. Then, the cells were washed and suspended again in the buffer. Thus, the amount of anthocyanin was analyzed by HPLC. The analysis is as follows.

Analysis flow:

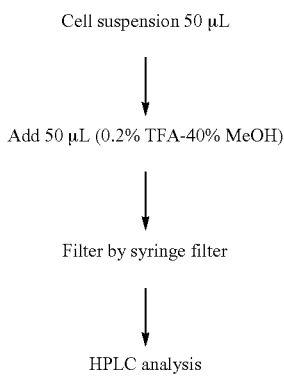

The condition of HPLC is as follows:
Column: YMC UltraHT Pro C18 dia.2.0×100 mm
Column temperature: 30 degrees Celsius
Eluent: A=0.3% TFA aqueous solution, B=acetonitrile
Gradient: 5% B (0 min)-5% B (0.60 min)-13% B (0.61 min)-15% B (3.00 min)-26% B (6.00 min)-90% B (6.20 min)-90% B (7.20 min)-5% B (7.40 min)-5% B (9.50 min)
Flow rate: 0.3 mL/min, Injection volume: 50 μL
Quantitative limit: 2 ng/mL (cyaniding-3-O-glucoside)
Reference documents: Exp. Eye Res, 83, 348 (2006)
J Agric. Food Chem, 49 1546 (2001)

(4-3) Test Result and Effect of the Working Example of Test Example 4

Figure 14:
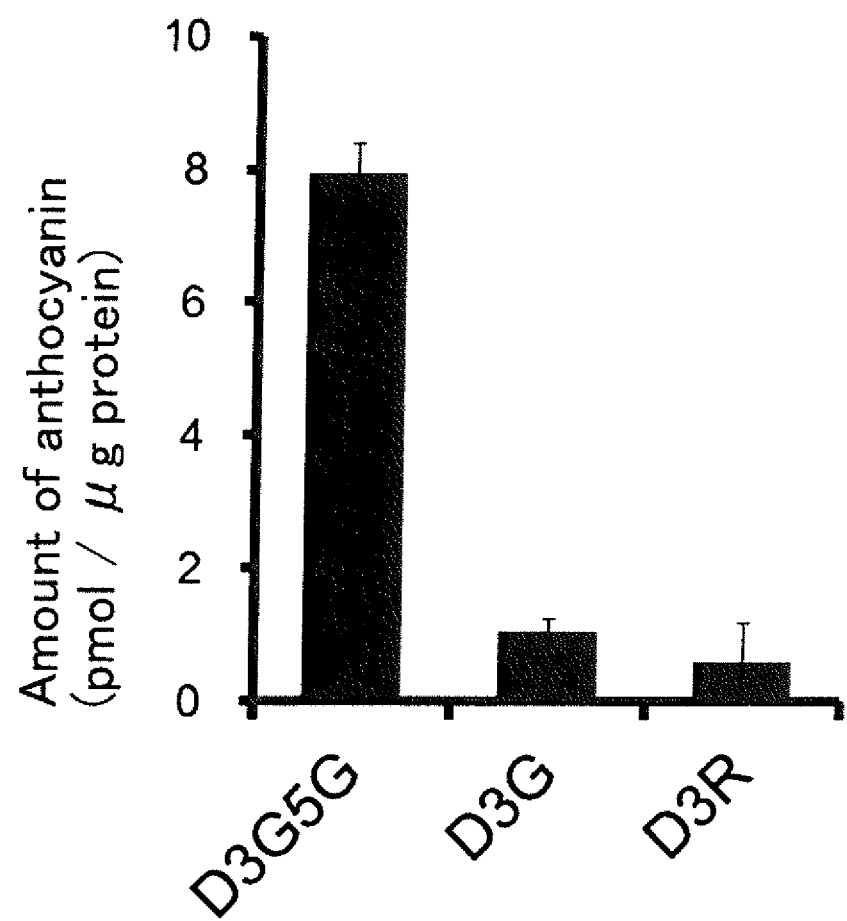
FIG. 14 is a graph showing the comparative incorporated amount of anthocyanin (delphinidin-3,5-diglucoside; D3G5G, delphinidin-3-glucoside; D3G, delphinidin-3-rutinoside; D3R) to the lacrimal cells.

FIG. 14 shows the result of the absorption test concerning the lacrimal cells of the active substance contained in the maqui berry extract.

As a result of comparing the amount of absorption of each anthocyanin (Mean±SE, n=6, delphinidin-3,5-diglucoside; D3G5G, delphinidin-3-glucoside; D3G, delphinidin-3-rutinoside; D3R) into the lacrimal cells, obviously delphinidin-3,5-diglucoside (D3G5G) as the particular substance of the maqui berry was absorbed by the lacrimal cells more than delphinidin-3-glucoside (D3G; substance contained in bilberry) and delphinidin-3-rutinoside (D3R: substance contained in cassis), thus verifying that the maqui berry extract is easily absorbed by the lacrimal cells and stored there, thus showing to be more effective against dry eye than the other anthocyanin substances.

The following charts show examples of the compounds for the prophylactic and therapeutic agent for dry eye of this invention. However, the compounds shown below are not limited to these examples.

Blending Example 1: Chewing Gums

| | |
|---|---|
| Sugar | 53.0 wt % |
| Gum base | 20.0 |
| Glucose | 10.0 |
| Starch syrup | 16.0 |
| Aroma chemical | 0.5 |
| Prophylactic and therapeutic agent for dry eye | 0.5 |
| | 100.0 wt % |

Blending Example 2: Gummies

| | |
|---|---|
| Reduction sugar | 40.0 wt % |
| Granulated sugar | 20.0 |
| Glucose | 20.0 |
| Gelatine | 4.7 |
| Water | 9.68 |
| Yuzu juice (*Citrus junos*) | 4.0 |
| Yuzu flavor | 0.6 |
| Pigment | 0.02 |
| Prophylactic and therapeutic agent for dry eye | 1.0 |
| | 100.0 wt % |

Blending Example 3: Candies

| | |
|---|---|
| Sugar | 50.0 wt % |
| Starch syrup | 33.0 |
| Water | 14.4 |
| Organic acid | 2.0 |
| Aroma chemical | 0.2 |
| Prophylactic and therapeutic agent for dry eye | 0.4 |
| | 100.0 wt % |

Blending Example 4: Yogurt (Hard Type/Soft Type)

| | |
|---|---|
| Milk | 41.5 wt % |
| Powdered skim milk | 5.8 |
| Sugar | 8.0 |
| Agar-agar | 0.15 |
| Gelatin | 0.1 |
| Lactic acid bacterium | 0.005 |
| Prophylactic and therapeutic agent for dry eye | 0.4 |
| Aroma chemical | Minute amount |
| Water | Rest |
| | 100.0 wt % |

Blending Example 5: Soft Drinks

| | |
|---|---|
| Fructose glucose solution | 30.0 wt % |
| Emulsifying agent | 0.5 |
| Prophylactic and therapeutic agent for dry eye | 0.3 |
| Aroma chemical | Appropriate amount |
| Distilled water | Rest |
| | 100.0 wt % |

Blending Example 6: Tablet-Shaped Sweets

| | |
|---|---|
| Sugar | 76.4 wt % |
| Glucose | 19.0 |

| | |
|---|---|
| Glycerine fatty acid ester | 0.2 |
| Prophylactic and therapeutic agent for dry eye | 0.5 |
| Distilled water | 3.9 |
| | 100.0 wt % |

Blending Example 7: Soft Capsules

| | |
|---|---|
| Brown rice germ oil | 47.0 wt % |
| Yuzu (*Citrus junos*) seed oil | 40.0 |
| Emulsifying agent | 12.0 |
| Prophylactic and therapeutic agent for dry eye | 1.0 |
| | 100.0 wt % |

Blending Example 8: Tablets

| | |
|---|---|
| Lactose | 54.0 wt % |
| Crystaline Cellulose | 30.0 |
| Starch splitting product | 10.0 |
| Glycerin fatty acid ester | 5.0 |
| Prophylactic and therapeutic agent for dry eye | 1.0 |
| | 100.0 wt % |

Blending Example 9: Eye Drops

| | |
|---|---|
| Ketotifen fumarate | 0.7 wt % |
| Azulene sodium sulfonate | 0.2 |
| Sodium cromoglycate | 9.8 |
| L-potassium aspartate | 8.5 |
| Allantoin | 3.0 |
| Tetrahydrozoline hydrochloride | 0.5 |
| Neostigmine methylsulfate | 0.05 |
| Benzalkonium chloride | 0.1 |
| Glycerin | 25.0 |
| Prophylactic and therapeutic agent for dry eye | 1.0 |
| pH adjuster | Appropriate amount |
| Distilled water | Rest |
| | 100.0 wt % |

INDUSTRIAL APPLICABILITY

As described above, this invention makes it possible to provide a prophylactic and therapeutic agent for dry eye, and an inhibitor to the deterioration of the lacrimal secretory ability, and an inhibitor to the generation of radical oxygen in lacrimal gland tissue, which contain new ingredients derived from the maqui berry, which is a safe food.

The invention claimed is:

1. A method for inhibiting generation of radical oxygen species in treatment of dry eye comprising:
   providing a maqui berry extract containing delphinidin-3,5-diglucocide as an active substance; and
   administering an effective amount of the maqui berry extract containing delphinidin-3,5-diglucocide to the person to accumulate the delphinidin-3,5-diglucocide in lacrimal gland tissue so as to decrease the deterioration of lacrimal secretion.

2. The method of claim 1, wherein the maqui berry extract contains 6 to 25% of delphinidin-3,5-diglucocide.

3. The method of claim 2, wherein the maqui berry extract contains 10 to 20% of delphinidin-3,5-diglucocide.

4. The method of claim 1, wherein the maqui berry extract is contained in chewing gum, gummies, candies, yogurt, soft drinks, tablet-shaped sweets, capsules, tablets, and eye drops.

5. The method of claim 1, wherein the administering step further comprises administering 0.5 to 5000 mg of the active substance per day.

6. The method of claim 5, wherein 0.5 to 3000 mg per day are administered.

7. The method of claim 5, wherein the administering step further comprises administering 4 to 20 mg/kg of the active substance per day.

* * * * *